(12) United States Patent
Boukhayma et al.

(10) Patent No.: US 12,040,807 B2
(45) Date of Patent: Jul. 16, 2024

(54) CYCLIC ADC WITH VOTING AND ADAPTIVE AVERAGING

(71) Applicant: Senbiosys, Neuchâtel (CH)

(72) Inventors: Assim Boukhayma, Neuchâtel (CH); Massimiliano Bracco, Le Landeron (CH); Antonino Caizzone, Milvignes (CH)

(73) Assignee: SENBIOSYS, Neuchâtel (CH)

( * ) Notice: Subject to any disclaimer, the term of this patent is extended or adjusted under 35 U.S.C. 154(b) by 0 days.

(21) Appl. No.: 17/576,681

(22) Filed: Jan. 14, 2022

(65) Prior Publication Data

US 2022/0231695 A1 Jul. 21, 2022

Related U.S. Application Data

(60) Provisional application No. 63/175,302, filed on Apr. 15, 2021, provisional application No. 63/138,049, filed on Jan. 15, 2021.

(51) Int. Cl.
*H03M 1/34* (2006.01)
*H03M 1/00* (2006.01)
*H03M 1/06* (2006.01)

(52) U.S. Cl.
CPC ......... *H03M 1/002* (2013.01); *H03M 1/0634* (2013.01)

(58) Field of Classification Search
CPC ...... H03M 1/0695; H03M 1/403; H03M 1/14; H03M 1/144; H03M 1/40; H04N 25/75; H04N 25/745; H04N 25/60; H04N 25/616; H04N 25/00; H04N 25/65; H04N 25/67

USPC .......................................... 341/155, 161, 163
See application file for complete search history.

(56) References Cited

U.S. PATENT DOCUMENTS

| | | | | |
|---|---|---|---|---|
| 4,691,190 A | * | 9/1987 | Robinson | H03M 1/442 341/97 |
| 4,760,376 A | * | 7/1988 | Kobayashi | H03M 1/162 341/172 |
| 5,416,485 A | * | 5/1995 | Lee | H03M 1/066 341/172 |
| 6,166,367 A | * | 12/2000 | Cho | H04N 25/00 348/308 |
| 6,888,568 B1 | * | 5/2005 | Neter | H04N 25/63 348/222.1 |

(Continued)

FOREIGN PATENT DOCUMENTS

JP 2013081093 A 5/2013

OTHER PUBLICATIONS

International Search Report and Written Opinion of the International Searching Authority, mailed on Apr. 20, 2022, from International Application No. PCT/IB2022/050323, filed on Jan. 15, 2022. 19 pages.

(Continued)

*Primary Examiner* — Linh V Nguyen
(74) *Attorney, Agent, or Firm* — HoustonHogle LLP

(57) ABSTRACT

A cyclic analog to digital converter for digitizing an output from a photoplethysmography sensor has a buffer amplifier for setting a voltage of the feedback capacitance. Additionally, digital averaging circuit is preferably provided for averaging the digital output from the cyclic analog to digital converter for the several conversions. Finally, voting logic is additionally provided for declaring the digital bits based on successive comparisons by the one or more comparators.

14 Claims, 15 Drawing Sheets

(56) References Cited

U.S. PATENT DOCUMENTS

| | | | | |
|---|---|---|---|---|
| 7,068,202 B2* | 6/2006 | Waltari | H03M 1/1245 | 327/158 |
| 7,164,379 B1* | 1/2007 | Rao | H03M 1/52 | 341/161 |
| 7,173,427 B1* | 2/2007 | Adachi | G01R 33/3621 | 324/318 |
| 8,004,435 B2* | 8/2011 | Waki | H03M 3/35 | 341/122 |
| 9,438,260 B1* | 9/2016 | Ebata | H03M 1/1038 | |
| 9,912,883 B1* | 3/2018 | Lee | H03M 1/56 | |
| 2002/0068859 A1* | 6/2002 | Knopp | A61B 5/1455 | 600/322 |
| 2008/0074304 A1* | 3/2008 | Horie | H03M 1/0695 | 341/155 |
| 2011/0254716 A1* | 10/2011 | Makihara | H03M 1/0695 | 341/172 |
| 2013/0069811 A1* | 3/2013 | Jones, III | H03M 1/403 | 341/163 |
| 2016/0043733 A1* | 2/2016 | Nezuka | H03M 3/464 | 341/143 |
| 2019/0215004 A1* | 7/2019 | Nezuka | H03F 3/45475 | |
| 2022/0407530 A1* | 12/2022 | Strandvik | H03M 1/0626 | |

OTHER PUBLICATIONS

Cao, C., et al., "A Time-Resolved NIR Lock-In Pixel CMOS Image Sensor with Background Cancelling Capability for Remote Heart Rate Detection," IEEE Journal of Solid-State Circuits, 54(4): 978-991 (2019).

Hain, N., et al., "A Capacitor Scaling and Capacitor Sharing Technique for Reducing Power Dissipation in Algorithmic ADCs," Analog Integr Circ. Sig. Process, 71: 333-335 (2012).

International Preliminary Report on Patentability, mailed on Jul. 27, 2023, from International Application No. PCT/IB2022/050323, filed on Jan. 15, 2022. 12 pages.

* cited by examiner

CYCLIC ADC WITH VOTING AND ADAPTIVE AVERAGING

RELATED APPLICATIONS

This application claims the benefit under 35 USC 119(e) of U.S. Provisional Application No. 63/138,049, filed on Jan. 15, 2021, and U.S. Provisional Application No. 63/175,302, filed on Apr. 15, 2021, both of which are incorporated herein by reference in their entirety.

BACKGROUND OF THE INVENTION

Nowadays, wearable devices, such as fitness trackers or smartwatches, with optical heart rate sensors, are becoming common.

The technology behind these sensors is called photoplethysmography (PPG), which is an optical measurement technique used to detect blood volume changes in living tissues. A PPG sensor requires few optoelectronics components, such as a light source, e.g. light-emitting-diode (LED) to illuminate the living tissue, a photodetector (PD) to track any light intensity variation due to the blood volume change and an analog front-end (AFE) for signal conditioning and processing. Today, the importance of PPG for medical monitoring is proven by the number of primary vital signs directly or indirectly that can be resolved by it.

The PPG signal is obtained by shining light from the LED at a given wavelength, in the visible or near-infrared range, into a human tissue, e.g. finger, wrist, forehead, ear lobes. The PPG sensor or photodetector detects the light transmitted through (transmissive PPG) or reflected (reflective PPG) from the tissue and transforms it into a photogenerated current. The detected signal, i.e. PPG signal, has two different components: a large DC (quasi-static) component corresponding to the light diffusion through tissues and non-pulsatile blood layers, and a small AC (pulsatile) part due to the diffusion through the arterial blood. The AC component is only a very small fraction (typically 0.2% to 2%) of the DC one, meaning the AC component is 500 to 50 times smaller than the DC component. This mostly depends on the body location and the LED wavelength and weakly on the skin tone. Such small AC/DC ratio is often called perfusion-index (PI) and ultimately sets one of the challenges for any PPG readout system. Indeed, the AC component carries most of the biomedical information. Low PI values lead to reduced signal fidelity, complicated signal processing schemes and larger power consumption.

State-of-the-art PPG sensors are discrete component systems or integrated circuits (IC) embedding a photosensitive area, an analog front end (AFE) and an analog-to-digital-converter (ADC). They are often designed to cope with the worst-case PI, translating into large dynamic range conditions and, as well, large ADC resolutions (above 15 bits).

SUMMARY OF THE INVENTION

To be able to obtain a valuable measurement with low power constraints and low signal amplitude, care is required in the design of the sensor and a very low power signal conditioning circuit which is able to guarantee stable and robust measurement results.

In addition, to target the largest application scenario, it is helpful to adapt the measurement to speed, power and accuracy requirements, even when every measurement is corrupted by noise, and uncorrelated signals superposed on the information to be extracted. To reduce effects of noise, averaging can be performed over many measurements.

Cyclic analog to digital converter architectures have advantages for PPG sensor systems. They can operate at low power. In addition, they are easy to adapt to different desired bit resolutions. Yet further innovation is required to improve performance. In that vein, a number of innovations are proposed including the accuracy with which these cyclic ADC's can be reset, their ability to address and minimize noise, and their ability to minimize undesired behavior when signal levels are near the ADC's internal thresholds.

In general, according to one aspect, the invention features a light to digital converter of a photoplethysmography sensor in which the converter comprises a sensor array and a cyclic analog to digital converter for receiving an output from the sensor array and for digitization as an input voltage.

In general, according to another aspect, the invention features a cyclic analog to digital converter for digitizing an output from a photoplethysmography sensor. The converter comprises an operational transconductance amplifier, an input capacitance for sampling an input voltage to the operational transconductance amplifier, a feedback capacitance providing feedback between an output and an input for the operational transconductance amplifier, and a buffer amplifier for setting a voltage of the feedback capacitance.

Two switches can be used for connecting both sides of the feedback capacitance to the buffer amplifier.

In addition, the switches can both be controlled by a clock that is active for determination of every bit of a conversion.

In general, according to another aspect, the invention features a cyclic analog to digital conversion system for digitizing an output from a photoplethysmography sensor. The system comprises a cyclic analog to digital converter for performing several analog to digital conversions on the same input voltage and a digital averaging circuit for averaging the digital output from the cyclic analog to digital converter for the several conversions.

The digital averaging circuit can comprise a storage device and a digital averaging circuit.

In addition, the digital averaging circuit might average at least 5, 10 or more conversions by the cyclic analog to digital converter.

In general, according to another aspect, the invention features a cyclic analog to digital converter for digitizing an output from a photoplethysmography sensor. The analog to digital converter comprises an operational transconductance amplifier, an input capacitance for sampling an input voltage to the operational transconductance amplifier, a feedback capacitance providing feedback between an output and an input for the operational transconductance amplifier, and one or more comparators for determining digital bits based on a voltage on the input capacitance. Voting logic is additionally provided for declaring the digital bits based on successive comparisons by the one or more comparators.

In general, according to another aspect, the invention features a method for digitizing in a photoplethysmography sensor comprising: detecting light with a sensor array and receiving an output from the sensor array at a cyclic analog to digital converter.

In general, according to another aspect, the invention features a method for digitizing an output from a photoplethysmography sensor comprising performing several analog to digital conversions on the same input voltage; and averaging the digital conversions.

In general, according to another aspect, the invention features a method for digitizing an output from a photoplethysmography sensor comprising generating successive bits of an analog to digital conversion with a cyclic analog to digital converter and declaring the digital bits based on successive comparisons by the one or more comparators based on most frequent digital bits for each bit of the multi bit conversion.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings.

DETAILED DESCRIPTION OF THE PREFERRED EMBODIMENTS

The invention now will be described more fully hereinafter with reference to the accompanying drawings, in which illustrative embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

As used herein, the term "and/or" includes any and all combinations of one or more of the associated listed items. Also, all conjunctions used are to be understood in the most inclusive sense possible. Thus, the word "or" should be understood as having the definition of a logical "or" rather than that of a logical "exclusive or" unless the context clearly necessitates otherwise. Further, the singular forms and the articles "a", "an" and "the" are intended to include the plural forms as well, unless expressly stated otherwise. It will be further understood that the terms: includes, comprises, including and/or comprising, when used in this specification, specify the presence of stated features, integers, steps, operations, elements, and/or components, but do not preclude the presence or addition of one or more other features, integers, steps, operations, elements, components, and/or groups thereof. Further, it will be understood that when an element, including component or subsystem, is referred to and/or shown as being connected or coupled to another element, it can be directly connected or coupled to the other element or intervening elements may be present.

It will be understood that although terms such as "first" and "second" are used herein to describe various elements, these elements should not be limited by these terms. These terms are only used to distinguish one element from another element. Thus, an element discussed below could be termed a second element, and similarly, a second element may be termed a first element without departing from the teachings of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Figure 1:
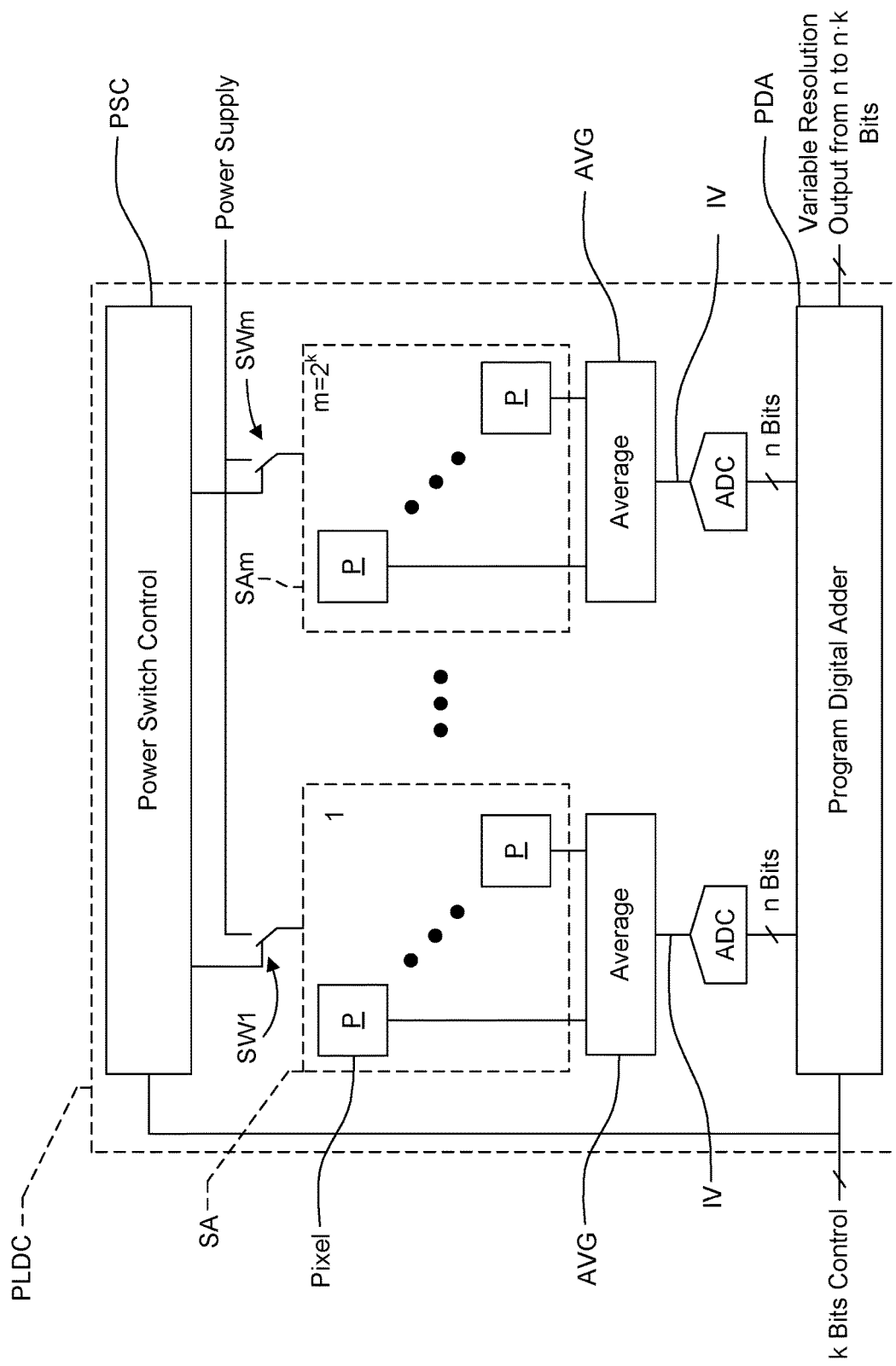
FIG. 1 is a schematic diagram of a programmable light to digital converter PLDC.

FIG. 1 is a schematic of a programmable light to digital converter PLDC.

The programmable light to digital converter PLDC operates to take the average of the response of several pixels P in each of several sensor arrays SA of light to digital converters. Each pixel can be an individual photodiode or can be macropixels combing the response of several photodiodes.

In more detail, a power switch control unit PSC energizes the light to digital converters with a corresponding set of switches SW1-SWm.

For each light to digital converters, an averaging unit AVG averages the response of the pixels of the sensor array SA to which it is dedicated. The output of each averaging unit AVG is the input voltage IV to be digitized by a corresponding analog to digital converter ADC. Then, a programmable digital adder unit PDA combines the output of each analog to digital converter ADC into a variable resolution output of n to n*k bits based on k control bits.

Figure 2:
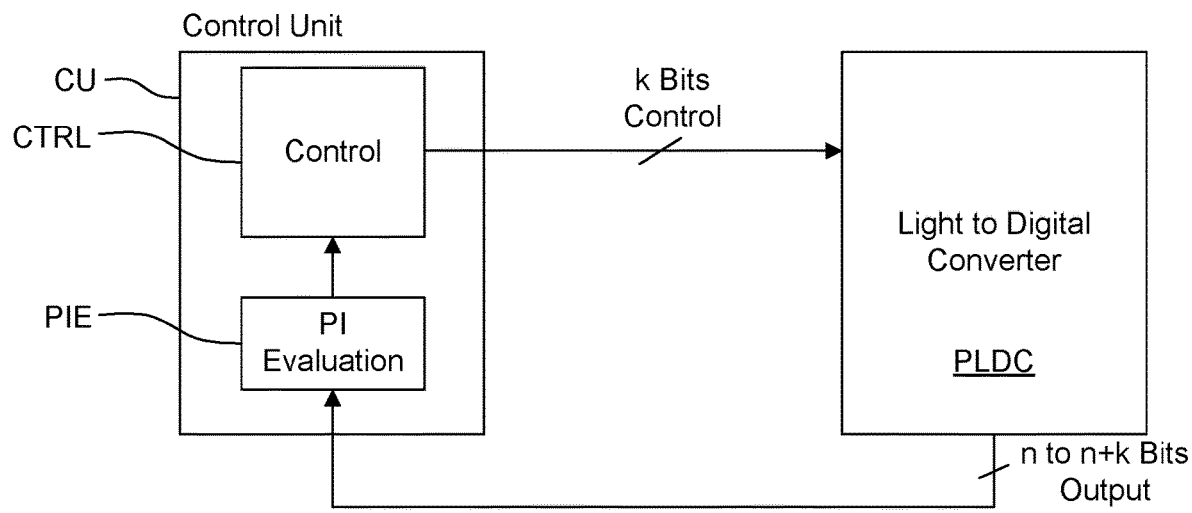
FIG. 2 is a schematic diagram of another programmable light to digital converter PLDC and its control unit.

FIG. 2 is a schematic of another programmable light to digital converter PLDC and its control unit CU.

The control unit CU includes a controller CTRL and a perfusion index evaluation unit PIE. In operation, the controller CTRL generates the k control bits based on the perfusion index determined by the perfusion index evaluation unit PIE.

This example provides more precision. A larger number of significant bits in the conversion is required but this consumes more power and even more time, depending on the algorithm for the conversion. Bit resolution must then be adapted to target the application scenario by the controller CTRL. Here, for example, the number of bits output from the light to digital converter PLDC is adapted based on k control bits from the control unit to thereby control the number of bits output, i.e., the resolution, of the light to digital converter PLDC between n output bits and n+k output bits.

Figure 3:
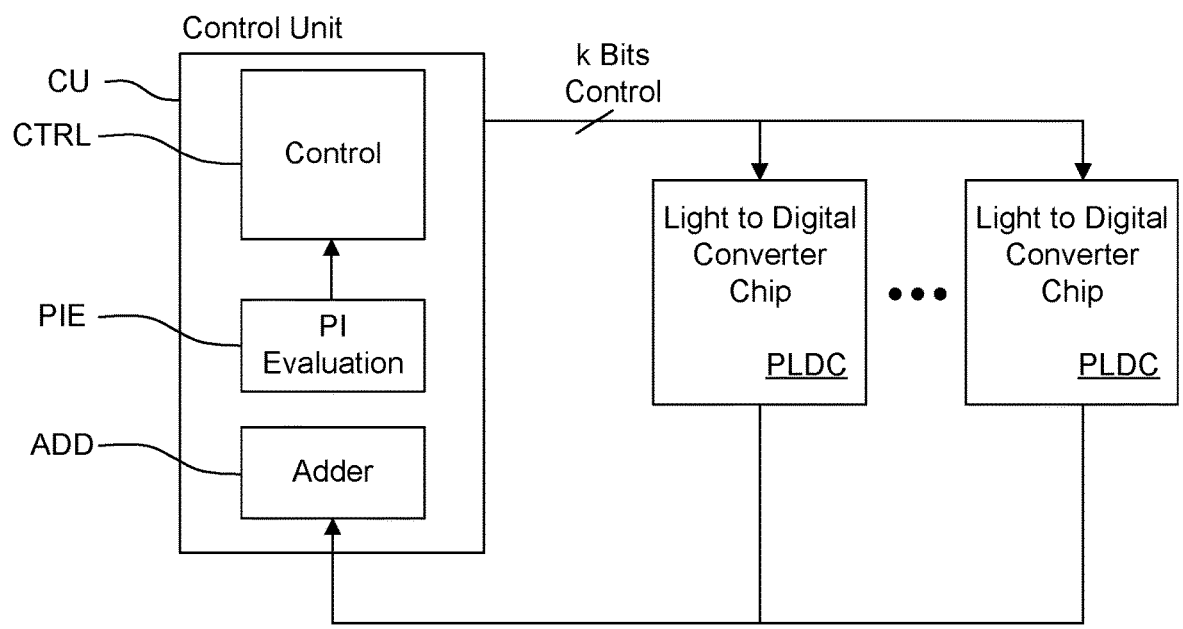
FIG. 3 is a schematic diagram of still another programmable light to digital converter PLDC and its control unit.

FIG. 3 is a schematic of still another programmable light to digital converter PLDC and its control unit.

Here, at the system level, more light to digital converters PLDC are provided, each having a variable resolution. Their outputs are added together by an adder ADD prior to evaluating the perfusion index.

A key element in the system is the way the conversion from analog to digital data is performed, the idea to reduce noise and adapt resolution.

In some aspects, the present invention generally concerns the analog to digital converters ADC employed in the one or more light to digital converters PLDC. They implement a cyclic algorithm and the cyclic structure is improved in terms of noise reduction and linearity by optionally using additional features: voting and/or adaptive averaging on digital results.

The adaptive averaging scheme is sensitive to power consumption which can be reduced where power constraints are more stringent with respect to the precision of the measurement or when the application requires more speed.

Voting algorithm guarantees more stability and higher confidence level even with reduced signal to noise ratio or higher conversion speed.

The following is a brief introduction to the cyclic ADC concept, timing diagram and conceptual schematic to illustrate the standard behavior.

Then block diagrams are provided to illustrate an exemplary implementation, along with simulations and results to demonstrate the validity of the additional algorithm for noise reduction and linearity improvement.

Cyclic ADC with Two Comparators

Figure 4:
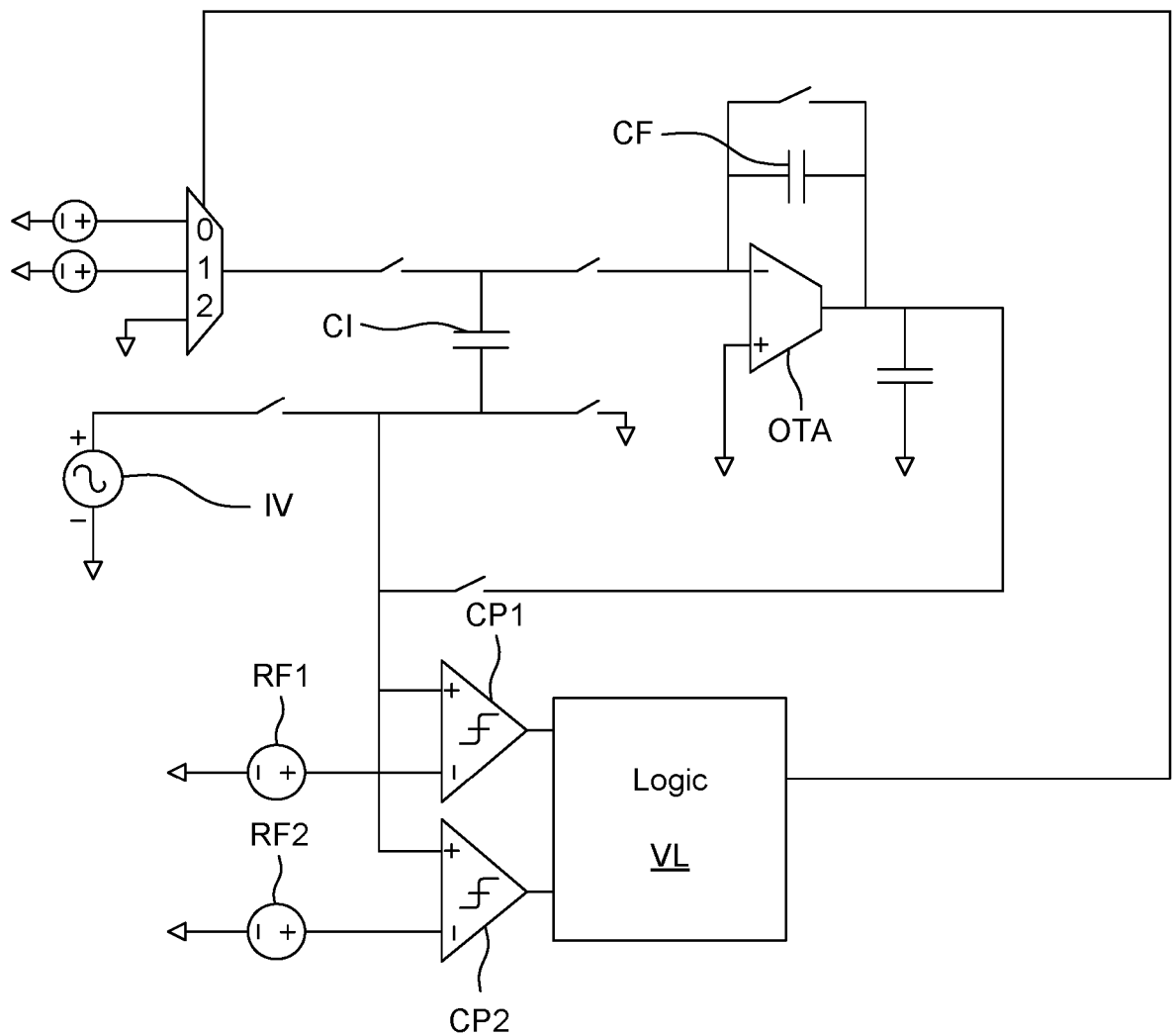
FIG. 4 is a circuit diagram of a cyclic analog to digital converter for digitizing the output from a photoplethysmography sensor.

FIG. 4 shows the elements for the standard cyclic analog to digital converter.

The cyclic analog to digital converter includes some active devices such as two comparators CP1, CP2, one operational transconductance amplifier OTA and some devices like switches and capacitances.

The key operations of a cyclic ADC are the sampling of the input voltage, the comparison with one or more thresholds and the multiplication by two of the difference between the sampled voltage and the reference.

The time behavior can be divided in different steps:
1. Input voltage IV from one or more pixels of the sensor arrays SAm is sampled.
2. Comparators CP1, CP2 decide which reference RF1, RF2 should be used to store charge on the input capacitance CI, the output of the comparators define the first bit of the conversion.
3. The feedback capacitance CF is reset to avoid any residual charge on it due to previous conversions.
4. The difference between the input voltage and the reference voltage determines the charge on the input capacitance CI, this charge is transferred to the feedback capacitance CF, since the ratio between input and feedback capacitance is 2, the voltage is multiplied by two at the operational transconductance amplifier OTA output.
5. From here on for every other bit of the conversion, the input to the comparators is taken from the OTA output directly.
6. The results of the comparators determine the second bit of the conversion and the reference is chosen.
7. The difference between OTA output and selected reference charges the input capacitance CI and the loop repeats itself from step 3 for every bit of the conversion string.

In this way, the cyclic ADC is useful for digitizing the output voltage from the sensor arrays since its resolution can be easily adapted on the fly and under the control of the control unit CU.

FIGS. 5-8 illustrate the sequence of the conversion.

Figure 5:
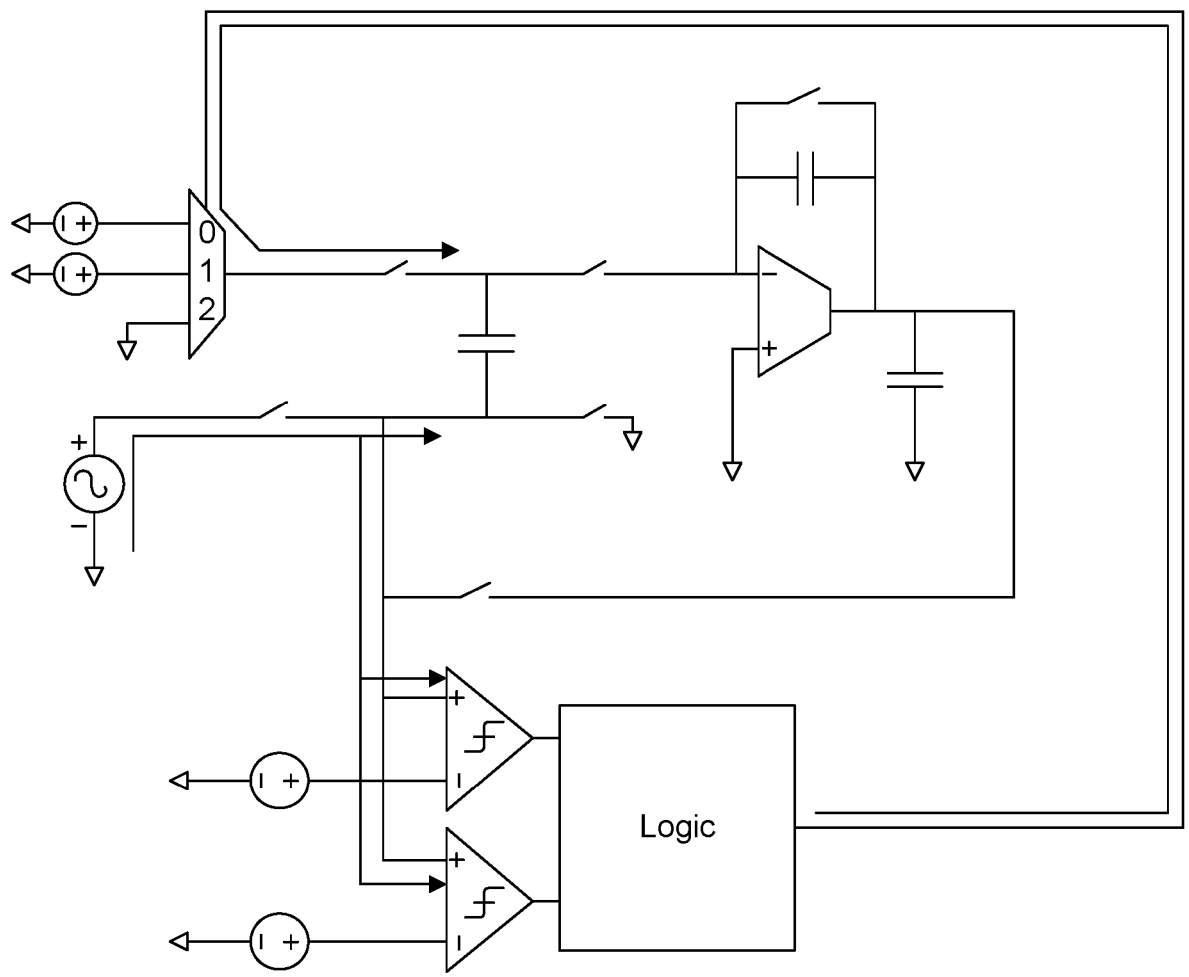
FIGS. 5-8 are circuit diagrams illustrating the sequence of the conversion by the cyclic analog to digital converter.

FIG. 5 illustrates step 1 and step 2 of the conversion. The input signal is sampled and reference decided. First, the most significant bit (MSB) of the conversion is determined.

The noted path is assured by state of the switches. The input voltage IV signal from sensor array is sampled. Then the comparators CP1, CP2 decide the reference for the other plate of the input capacitance CI. This first decision of the comparators is the MSB of the final conversion result.

Figure 6:
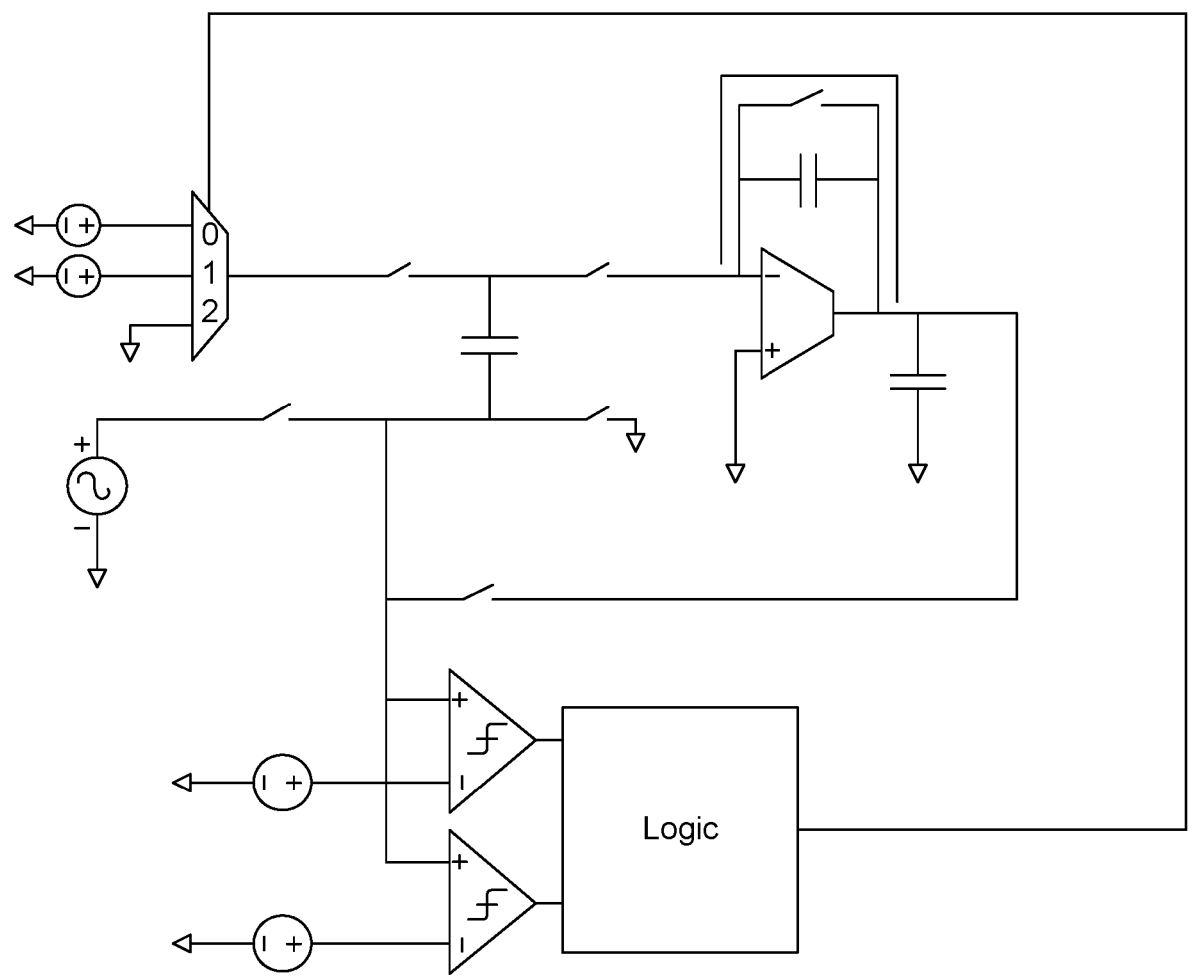

FIG. 6 shows the reset of the feedback capacitance CF. During this reset, the OTA is isolated from the input.

Figure 7:
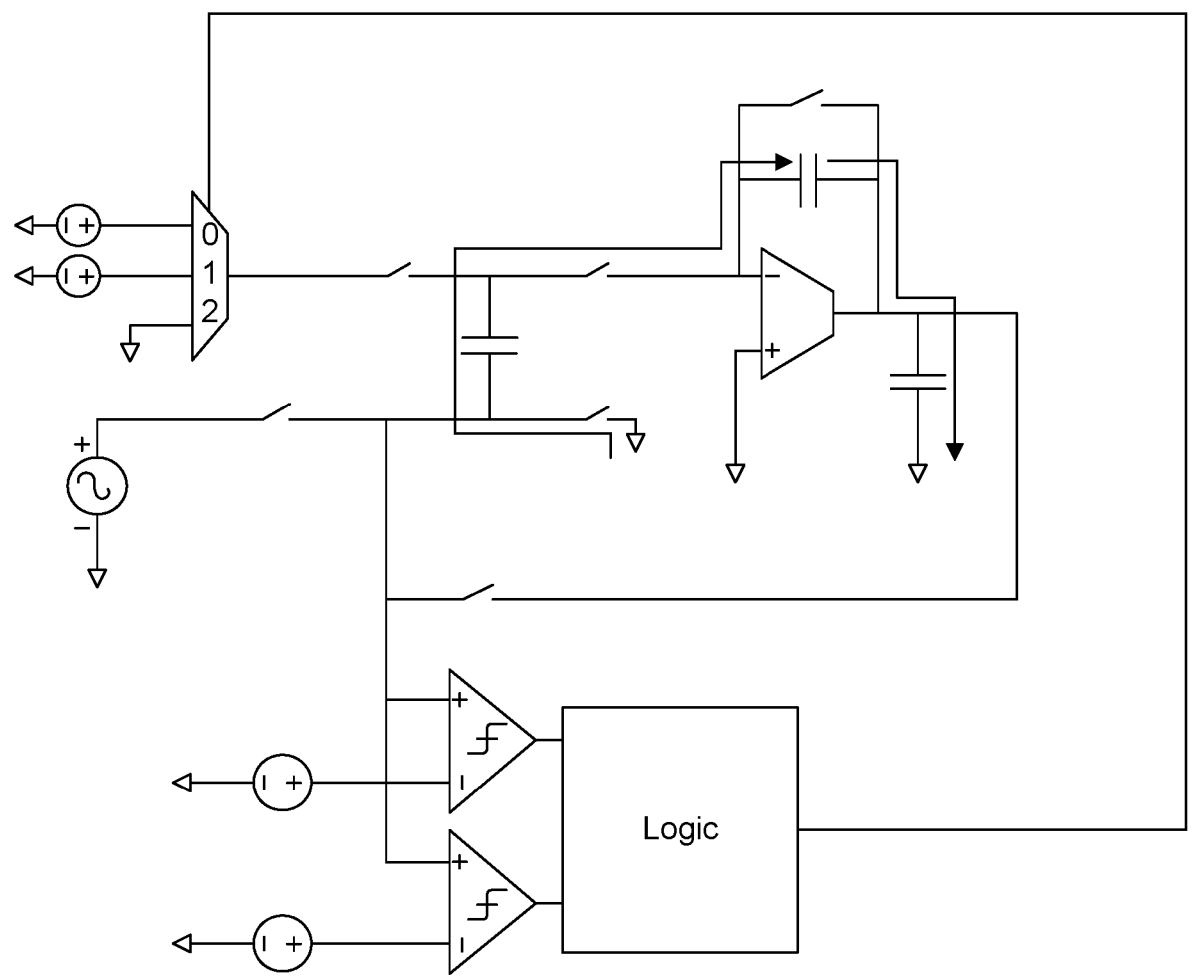

FIG. 7 shows step 4. The charge of the input capacitance CI is transferred to the feedback capacitor CF and a multiplication by two is performed since the feedback capacitance CF is two times smaller compared to the input capacitance CI. This operation is necessary since it next determines the second bit of the conversion. Therefore the residual voltage must be multiplied by two to be compared with the same threshold used for the MSB.

Then the loop starts over to reset and then charge the feedback capacitance CF and the comparators define the next bit until the required accuracy is reached based on the control bits from the control unit CU.

Figure 8:
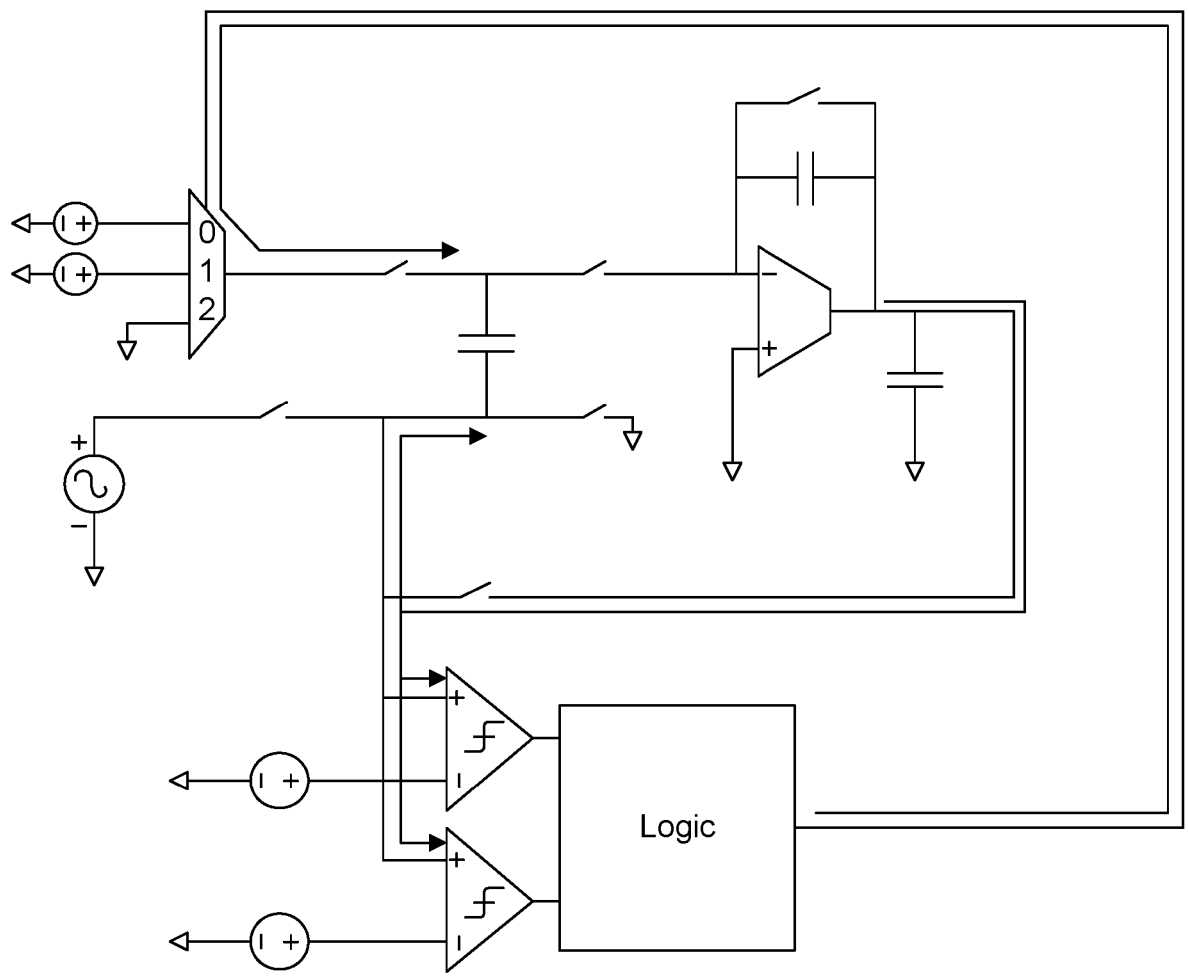

FIG. 8 shows steps 5 and 6. The input to the comparators is the result of the multiplication from the OTA.

In this implementation there are two threshold voltages RF1, RF2. While the same result could be achieved with one threshold only, having an additional reference built by analog circuitry provides the ability to reduce power consumption and achieve more linearity. Every time the charge on the input capacitance is reduced compared to one threshold case, the OTA must give less current to the feedback capacitance.

Linearity is also a beneficial effect of these two thresholds because the OTA dynamic range can be reduced since the additional threshold reduces the distance to the input signal.

Figure 9:
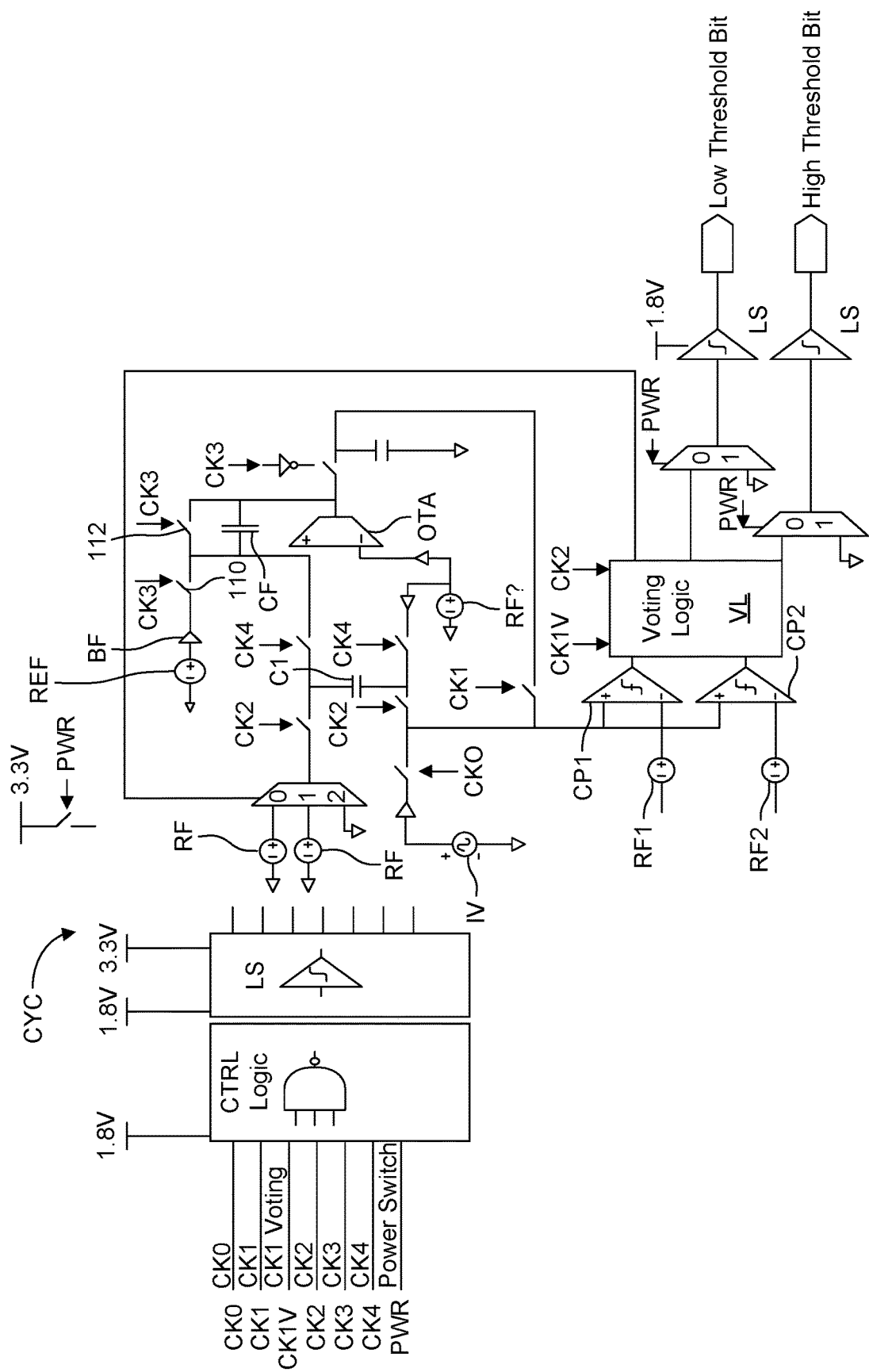
FIG. 9 is a circuit diagram of a cyclic analog to digital converter for digitizing the input voltage output from a photoplethysmography sensor with a buffer for resetting the feedback capacitance, according to the present invention.

FIG. 9 shows a complete cyclic analog to digital converter CYC which has been constructed according to the principles of the present invention.

In this example, there are the blocks for the basic required tasks but also some additional blocks like level shifters LS to deal with different voltage levels from logic which works at lower voltage.

For power management, an important parameter to take into account is of course power and the switch to cut power when ADC is inactive. This requires also some additional considerations to avoid any floating or unpredictable voltage level signals, for this reason the shifters are preferably directly and continuously powered by the analog supply.

Voltage reference and sampling is performed by buffers with very low loss and offset voltage.

To implement in a very efficient way the reset of the feedback capacitance CF an additional buffer BF and a reference voltage source REF is used to increase speed and assure a very good discharge of this capacitance in a very short time. In this example, clock3 controls its corresponding switches 110, 112 to connect the reference voltage source REF through the buffer amplifier BF to both sides of the feedback capacitance CF.

In one example, all the switches are in fact controlled by a rapid clock of 50 MHz and this frequency can increase to 80 MHz or more in some implementations. As a result, it is important to give additional current to reset the feedback capacitor quickly, since a partial discharge would introduce non linearity and error to the conversion.

Figure 10:
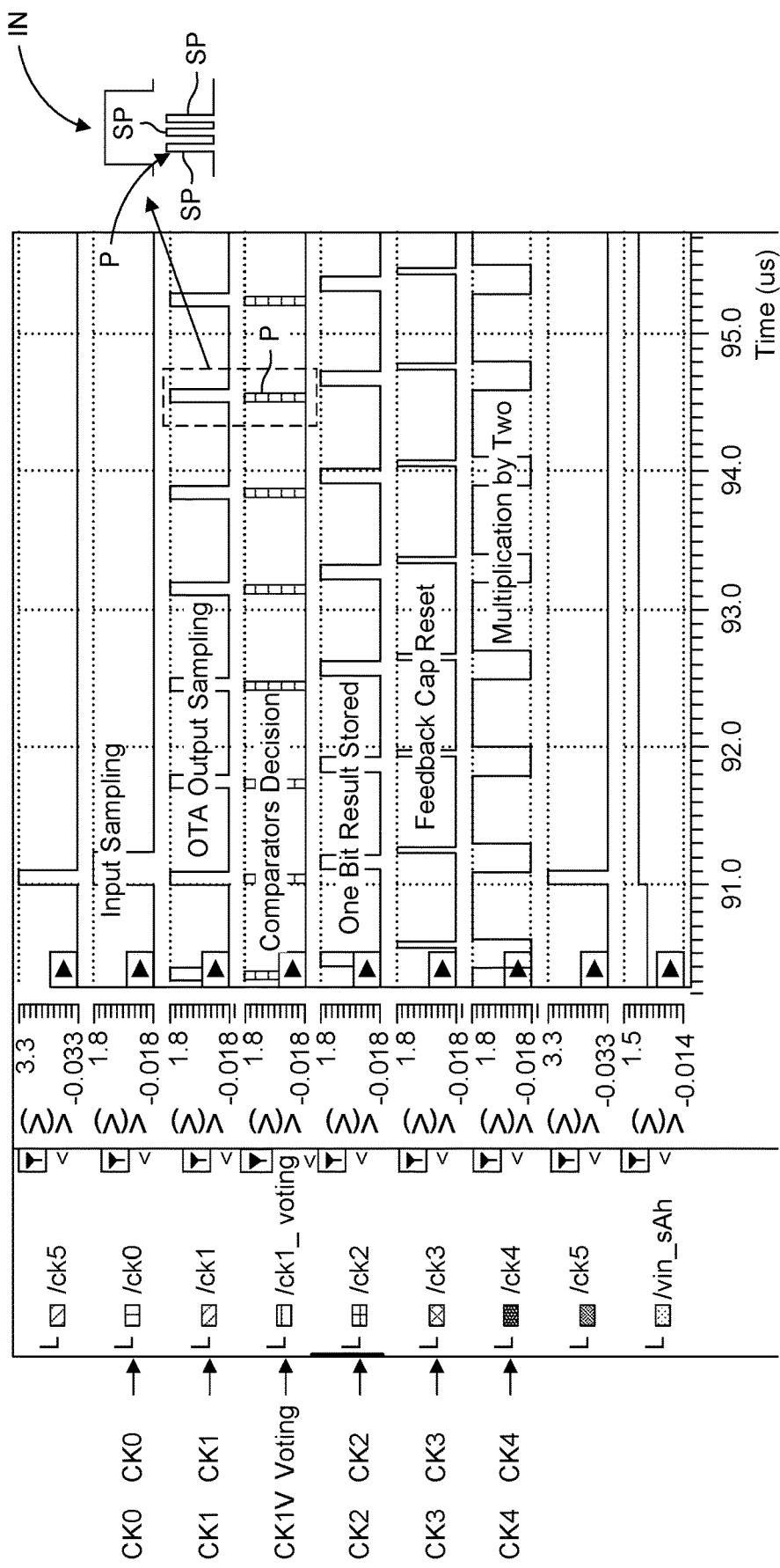
FIG. 10 is a timing diagram showing the various clocks required for the cyclic analog to digital converter.

FIG. 10 shows the various clocks required for the different steps of the conversion. These clocks activate switches in the right order.

Figure 11:
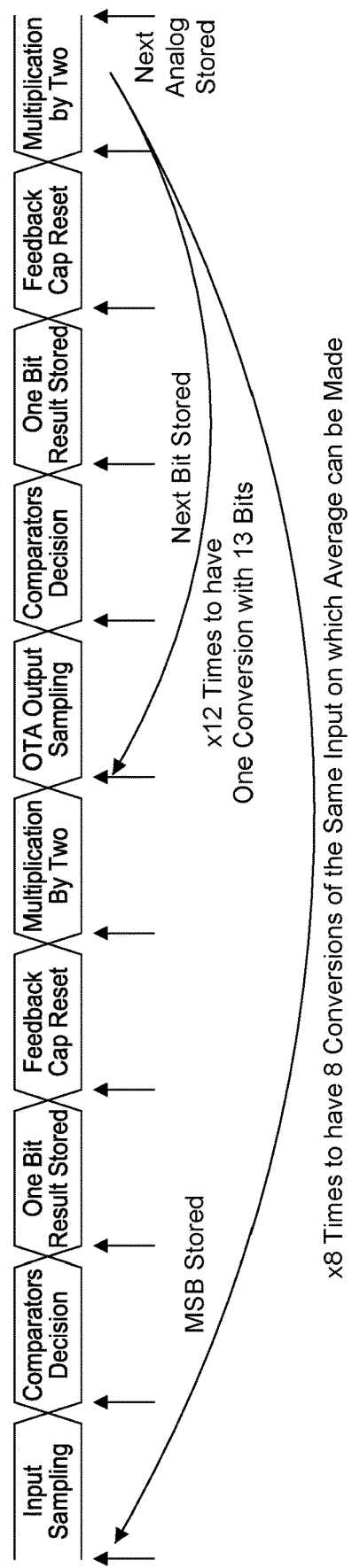
FIG. 11 is a timing diagram showing the operation over time to generate the various bits of the conversion.

FIG. 11 shows how the clocks drive completely the steps in the conversion and the charge transfers. The entire process from analog sampling to digital bit can be divided looking at the clock edges.

The example provides for the successive steps for the conversion and the recursive loops to have 13 bits for an analog to digital conversion and the loop on a single analog sample to provide 8 digital data on which averages can be performed.

Noise Reduction and Linearity Increase

The signal from one or more pixels of light to digital converters LDCm is always contaminated by interferences which can compromise the precision of the transduction and therefore the precision of the measurements. Interferences can be removed or attenuated depending on their characteristics. When the interference has an uncorrelated behavior with respect to the signal, this can be categorized as white noise and averaging is a powerful algorithm for reducing the amplitude of this interference.

The cyclic ADC samples the input signal on a capacitance. It thus makes an integration for all the time that the capacitance is connected to the input signal from the one or more pixels. This has the effect of decreasing white noise level from the sensor. To improve the signal to noise ratio, the value of the capacitance can be increased because the dependence of the output noise is inversely proportional to the capacitance. This change, however, also implies a longer time to reach the same voltage signal and finally a bigger power consumption because the current required from the OTA during multiplication by two is then bigger because of the increased charge cumulated.

Adaptive Averaging

To avoid these negative impacts, an adaptive average is performed on the digital results of the conversion by the ADC.

A relatively small input capacitance CI is used at the input. Then the circuit performs many conversions on the same analog signal to reduce white noise. It is possible to adapt the number of conversions that are averaged when a faster conversion is required over a decreased precision. In general, the input capacitance CI is large enough to reduce the kTC noise on that capacitor. But thanks to the digital averaging one can use smaller input capacitance allowing faster analog operation (digital averaging reduces the extra noise coming from the smaller capacitor).

In this way power consumption is reduced thanks to the smaller input capacitance CI to charge and it is still possible to get a better signal to noise ratio tailored to the accuracy needed by the application. When a fast conversion is required, it can be provided because of the small input capacitance.

Figure 12:
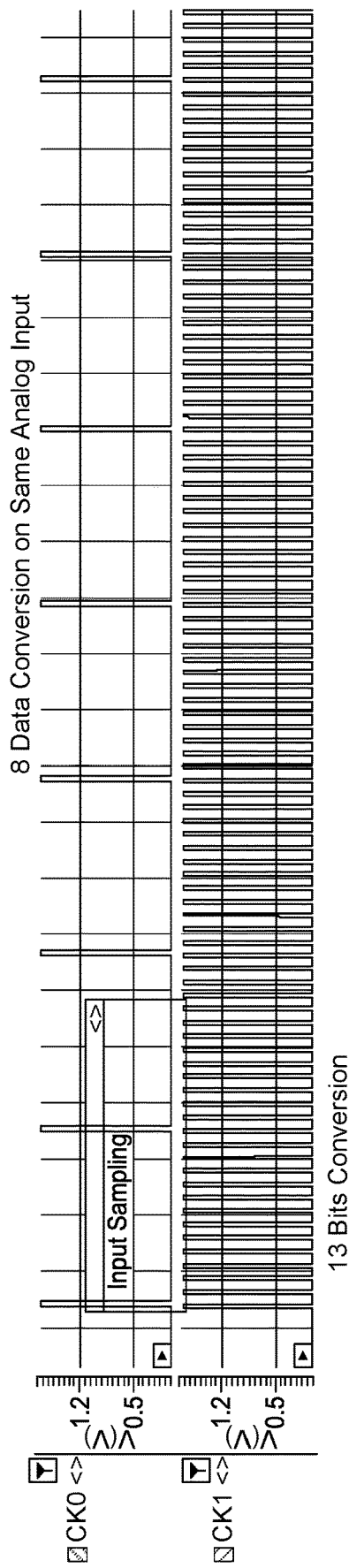
FIG. 12 is a timing diagram showing several conversions on the same analog input value from the photoplethysmography sensor by the cyclic ADC to perform adaptive averaging.

FIG. 12 shows several conversions on the same analog input value. The clock waveforms show the sampling of the input data many times. At every clock 0, a new conversion is done on the same input data. The digital side performs the average of the results. The number of averaged data can be adapted to have more conversion speed, in this case it takes around 60 microseconds to convert a sampled data from the sensor.

Figure 13:
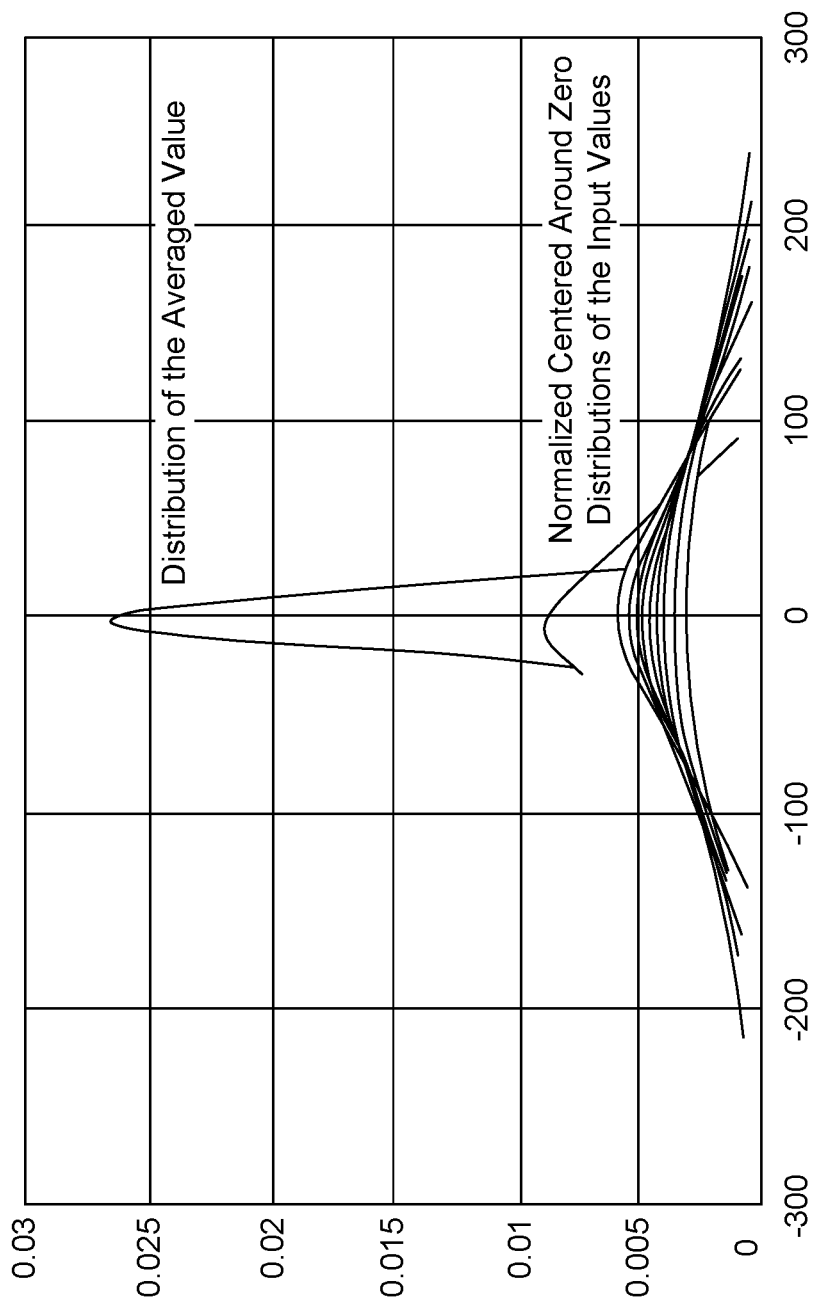
FIG. 13 is a plot showing how the averaging affects the Gaussian distribution.

The input data is perturbated by white noise, every sample is therefore slightly different to the previous and successive one. A Gaussian distribution represents very well this situation. The average over the conversion reduces the spread of this Gaussian distribution as illustrated by the calculation performed on at least 4 conversions and preferably 10 or more conversions of the same noisy analog input as shown in FIG. 13.

To get the same results, a larger capacitance would be required, which reduces speed and consumes more power. It is impossible to increase speed for faster conversions at reduced precision.

Figure 14:
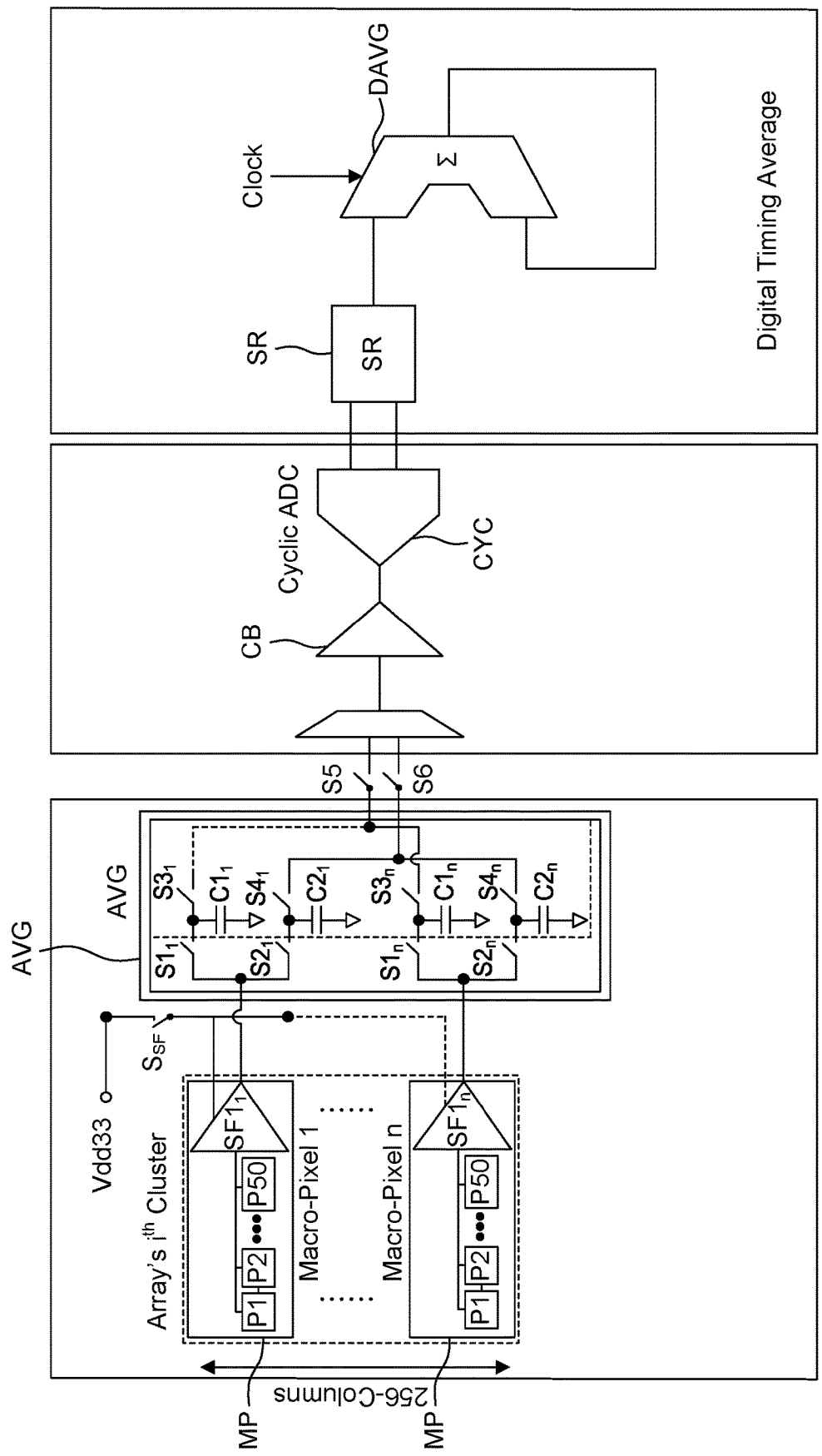
FIG. 14 is a schematic circuit diagram showing an exemplary system architecture employing multiple conversions of the same analog value followed by digital averaging.

FIG. 14 shows an exemplary system architecture employing multiple conversions of the same analog value followed by digital averaging.

The system operates in both the analog/digital domains and performs averaging in both. It employs spatial averaging in the use of n macropixels MP, which each comprise several to many separate pixels. The outputs of the macropixels MP are averaged in the analog averaging circuit AVG.

In one detailed implementation, a first averaging process is performed at each cluster then at column level where 50 pixels share their charge.

Ambient light is also preferably sampled and then subtracted by the total signal.

LED is pulsed and this generates the signal charge superposed to ambient light charge, and of course, the two signals are averaged between all the columns in a common big capacitance made of all the column capacitances in parallel.

This average held on the column capacitances is then provided to the cyclic ADC CYC via a converter buffer CB and digitized using the described cyclic ADC CYC.

In addition, adaptive timing average is also employed in the digital domain. Specifically, the 12 bit output from the cyclic ADC CYC is held by the SR flip flop SR and then its running average is calculated by the digital timing averaging unit DAVG. This approach provides power improvements and adds flexibility to the system because the averaging is adapted to the application requirements in term of accuracy or signal to noise ratio and the conversion time will be optimum for every application.

Voting Algorithm to Increase Linearity

Averaging is effective when the input noise is uncorrelated to the sampled data. When this situation occurs the operation of averaging reduces the amplitude of noise.

A real comparator can produce a wrong result when the input voltage is close to the threshold, this means the output value does not reflect correctly if the input is above or below level of threshold.

During a conversion there is the possibility for the input to be close to one of the thresholds. Because of the multiplication by two, there is an increase to the input voltage to the comparators at every clock. If an error is produced in the conversion, this error can be viewed as an interference, like noise. And this error is correlated to the input signal. Thus, there are indeed some voltage levels which are more prone to this kind of error and the conversion is then corrupted.

In this case the noise is no longer white noise and averaging cannot improve the results. The following describes additional voting circuitry that operates on the digital data to improve the robustness of the comparators and then increase the linearity of the conversion.

Referring back to FIG. 10, the inset IN show the detailed time behavior of voting clock CK1V. Each pulse P comprises 3 separate subpulses SP. The voting process is active in the "comparators decision" step. Just after the input sampling, the comparators are active for three cycles thanks to the voting clock subpulses which provide three edges for the repeated comparison.

Every time the input to a comparator is close to the threshold the output result is affected by every kind of fluctuation on the supply, temperature, output parasitic capacitance. Hence the result can be stochastic.

Nevertheless, if the conversion is repeated, the result is more likely to be correct because the probability to be in a point where supply or interferences are quiet is more likely to happen. Voting leverages this assumption.

The output of the comparator is stored three times and the result is the more frequent one, if there is a mismatch on the result the other two results are taken as correct.

Figure 15:
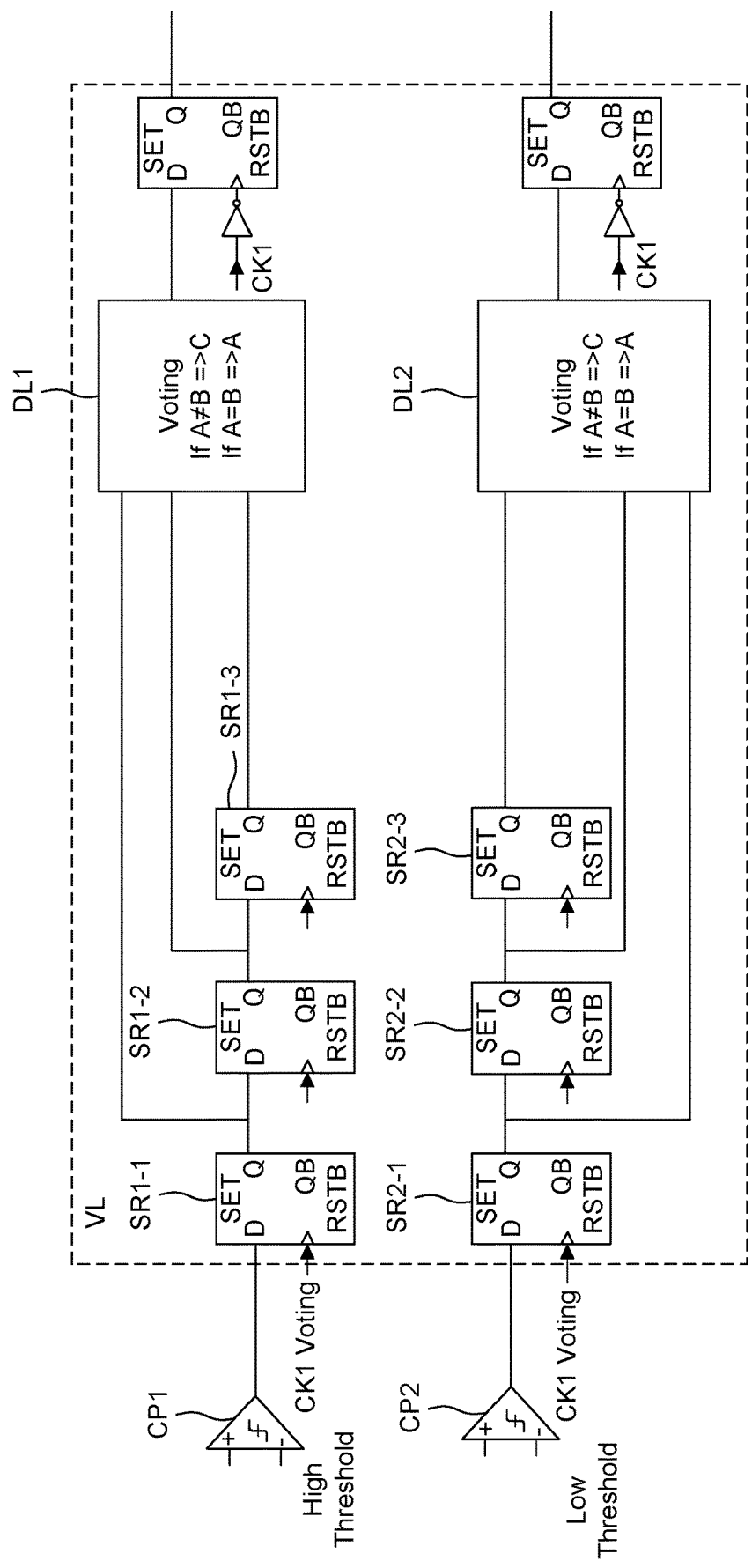
FIG. 15 is a circuit diagram showing the voting logic.

FIG. 15 shows the construction of the voting logic VL. It includes three memory elements for the output of both of the comparators CP1, CP2. These memory elements are clocked by the voting clock CK1V. Thus for the determination of each bit of the ADC output, three comparisons are stored for each of the comparators CP1, CP2. This storage is performed by a first set of three SR flip flops SR1-1, SR1-2, SR1-3 for the first comparator CP1 and a second set of three SR flip flops SR2-1, SR2-2, SR2-3 for the second comparator CP2. The decision logic DL1, DL2 for each comparator determines the most frequent results held in each of the corresponding three storage elements: SR1-1, SR1-2, SR1-3 for first comparator CP1, SR flip flops SR2-1, SR2-2, SR2-3 for the second comparator CP2. The decision logic DL1, DL2 then each output the more frequent bit.

To perform this decision the digital circuit has been implemented close or inside the ADC block to reduce the communication load to the digital blocks.

Figure 16:
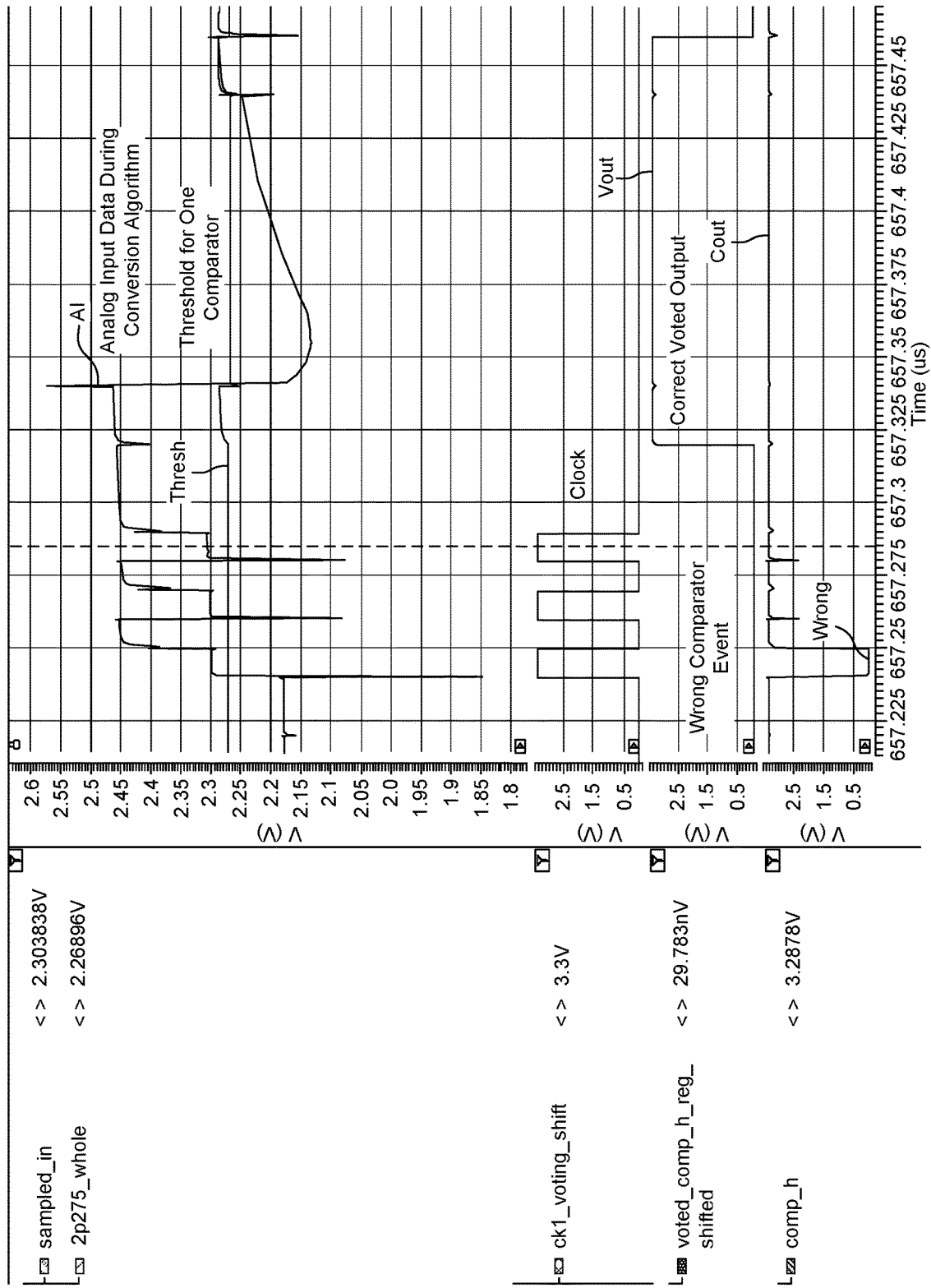
FIG. 16 is a timing diagram showing the waveforms from a simulation illustrating the operation of the voting.

FIG. 16 shows the timing waveforms from a simulation. The voting is effective to reduce error and therefore maintain linearity of the output data.

The simulation shows how the analog input AI to the comparator is always larger than the threshold THRESH during the comparator activation by the clock. The input is also quite close to the threshold and this generates a first wrong result WRONG.

The comparison is done two more times and in this case the results are correct VOUT. Voting circuitry decided then to take the logic one, hence masking the mistake.

During the conversion, this error cannot be anticipated. Therefore there could be a mistake in the MSB of the conversion with a big impact on the conversion. In this case averaging the results would not improve the result since an error on the MSB would require a large number of averages and is most likely the error would reappear because the voltage levels would be again close to the thresholds.

Nevertheless, the voting corrects the result then keeping the output linear with a very reduced overhead of the digital circuitry and reduced additional power consumption.

Cyclic Algorithm for Analog to Digital Conversion: Noise Modeling

Noise is distributed on switches, transistors, resistances, and it is possible to model their effects to concentrate noise sources in few points of the circuit: input, OTA and comparators references.

These noise sources can be voltage or current sources depending on the position in the circuit: at comparators input there can only be voltage sources because of the infinite input impedance model, OTA is a current source therefore noise is added in parallel as current source, all these sources have similar characteristics: all of them have a white noise distribution with a certain standard deviation or RMS value.

Noise on input and OTA output have the same effects on the digital data. For every input, the digital conversion shows a Gaussian distribution with similar standard deviation. Signal on OTA output has also a Gaussian distribution and its standard deviation does not depend on the input sampled value.

Noisy comparator references introduce fluctuations only when the inputs are closed to the nominal references. Digital data are spread only when, during the conversion history, the input to comparators are closed to their references.

It is important to understand noise sources impacts on digital conversion because there are different noise reduction strategies available to reduce spread.

Regarding the order of magnitude for the noise RMS value: input noise 90 u V RMS (1 k Ohm resistance at 27° C. 500 M Hz bandwidth), OTA output noise RMS around 200 u V-300 u V, regarding the noise level for the references, a 1 k Ohm resistance was used as noise source for 500 M Hz bandwidth to get around 90 u V RMS.

The comparators references noise level is important when the input on the other terminal gets closed to them, the effectiveness of the voting is related to this gap, and a bigger noise level increases the probability of having fluctuations but voting on three bits should be enough for a wide range of input values.

The digital value suffers, of course, a fluctuation and the standard deviation for this is around 20-30 decimal, quite low compared to the digital range with 13 bits. The average algorithm reduces the spread further depending on the number of averaged data.

Noise Reduction Algorithms: Adaptive Average

The noise can be characterized by Gaussian distribution around an average value and this distribution is symmetric. Positive and negative values have equal probability to occur. Bigger values are less probable to occur in a time record of the signal. To compensate for these positive and negative values, averaging over a longer time window because big spreads occur rarely, waiting more to compensate for them with a longer average time is required.

A long average time can be obtained in analog with larger capacitances increasing current consumption and conversion time, it is then almost impossible to adapt this time with the required accuracy demanded by the application since the heart rate is less demanding in accuracy, for instance, compared to SPO2 measurements.

The same random spread is observable on the digital data with similar distribution behavior, then the average introduced on digital data where it is much easier to adapt to the accuracy required: it is a matter of defining how many data must be averaged and adjust the number of bits for the registers.

The standard deviation can then be reduced increasing the number of sampled data per conversion.

Noise Reduction Algorithms: Voting

Inputs to the comparators change during the conversion history of a sampled data. This is due to the cyclic algorithm as described above.

Some samples are converted without any variations in the digital result and others, on the contrary, can have significant spread. This can be understood looking at the analog values at the comparators input: when they are closed, the presence of noise generated different results for the same repeated comparison.

Voting is a digital algorithm which evaluates the redundancy or repeated occurrence of a bit value and decides to assign the more frequent bit to the final output result. The number of bits required for the voting can be decided based on the spread of the digital data, in this case; it was observed that 3 bits are enough to reduce or completely remove the variability of the digital data.

While this invention has been particularly shown and described with references to preferred embodiments thereof, it will be understood by those skilled in the art that various changes in form and details may be made therein without departing from the scope of the invention encompassed by the appended claims.

What is claimed is:

1. A cyclic analog to digital converter for digitizing an output from a photoplethysmography sensor, the analog to digital converter comprising:
    an operational transconductance amplifier;
    an input capacitance for sampling an input voltage to the operational transconductance amplifier;
    a feedback capacitance providing feedback between an output and an input for the operational transconductance amplifier; and
    a buffer amplifier for resetting a voltage of the feedback capacitance to remove any residual charge on the feedback capacitance.

2. A cyclic analog to digital converter as claimed in claim 1, further comprising two switches for connecting both sides of the feedback capacitance to the buffer amplifier.

3. A cyclic analog to digital converter as claimed in claim 2, wherein the switches are both controlled by a clock that is active for determination of every bit of a conversion.

4. A cyclic analog to digital converter as claimed in claim 1, further comprising:
    a digital averaging circuit for averaging a digital output.

5. The system of claim 4, wherein the digital averaging circuit comprises a storage device and a digital averaging circuit.

6. The system of claim 4, wherein the digital averaging circuit averages at least 5 conversions by the cyclic analog to digital converter.

7. The system of claim 4, wherein the digital averaging circuit averages at least 10 conversions by the cyclic analog to digital converter.

8. A cyclic analog to digital converter for digitizing an output from a photoplethysmography sensor, the analog to digital converter comprising:
    an operational transconductance amplifier;
    an input capacitance for sampling an input voltage to the operational transconductance amplifier;
    a feedback capacitance providing feedback between an output and an input for the operational transconductance amplifier; and
    one or more comparators for determining digital bits of the output from the photoplethysmography sensor based on a voltage on the input capacitance; and
    voting logic for declaring each of the digital bits of the output from the photoplethysmography sensor based on successive comparisons by the one or more comparators for each of the bits; wherein the output of the one or more comparators is stored at least three times for each bit and the voting logic selects the more frequent bit output for each bit.

9. The converter of claim 8, wherein the voting logic comprise a series of 1 bit storage devices and decision logic that outputs frequent digital bits for each bit of the multi bit conversion.

10. A cyclic analog to digital converter as claimed in claim 1, further comprising a digital averaging circuit for averaging the digital output from the operational transconductance amplifier.

11. A cyclic analog to digital converter as claimed in claim 10, wherein the digital averaging circuit comprises a storage device and a digital averaging circuit.

12. A cyclic analog to digital converter as claimed in claim 11, wherein the digital averaging circuit averages at least 5 conversions.

13. A cyclic analog to digital converter as claimed in claim 1, further comprising switches controlled by a clock.

14. A cyclic analog to digital converter as claimed in claim 13, wherein the clock operates at 50 MHz or more.

* * * * *